(12) United States Patent
Zhang

(10) Patent No.: US 10,307,037 B2
(45) Date of Patent: Jun. 4, 2019

(54) SHOE DEODORIZING DEGERMING DEHUMIDIFIER AND SHOE DEODORIZING DEGERMING DEHUMIDIFYING METHOD

(71) Applicant: SHENZHEN LIFEN TECH CO., LTD, Shenzhen, Guangdong (CN)

(72) Inventor: Liwen Zhang, Guangdong (CN)

(73) Assignee: SHENZHEN LIFEN TECH CO., LTD, Shenzhen (CN)

( * ) Notice: Subject to any disclaimer, the term of this patent is extended or adjusted under 35 U.S.C. 154(b) by 486 days.

(21) Appl. No.: 15/147,880

(22) Filed: May 5, 2016

(65) Prior Publication Data

US 2016/0242620 A1 Aug. 25, 2016

Related U.S. Application Data

(63) Continuation of application No. PCT/CN2015/081014, filed on Jun. 8, 2015.

(30) Foreign Application Priority Data

Dec. 17, 2014 (CN) .......................... 2014 1 0790351

(51) Int. Cl.
*A61L 2/20* (2006.01)
*F26B 9/00* (2006.01)
*A47L 23/20* (2006.01)

(52) U.S. Cl.
CPC .............. *A47L 23/20* (2013.01); *A61L 2/202* (2013.01); *F26B 9/003* (2013.01); *A61L 2202/11* (2013.01); *A61L 2202/20* (2013.01)

(58) Field of Classification Search
CPC .......... F26B 9/003; A47L 23/20; A61L 2/202; A61L 2202/20; A61L 2202/11
See application file for complete search history.

(56) References Cited

U.S. PATENT DOCUMENTS

| 7,614,168 B1* | 11/2009 | Zummer | ............ A61H 15/0078 |
| | | | 36/141 |
| 2003/0152480 A1* | 8/2003 | Sham | ...................... A61L 2/202 |
| | | | 422/28 |

(Continued)

FOREIGN PATENT DOCUMENTS

| CN | 2836719 Y | 11/2006 |
| CN | 101366963 A | 2/2009 |

(Continued)

OTHER PUBLICATIONS

International Search Report of PCT Patent Application No. PCT/CN2015/081014 dated Sep. 22, 2015.

*Primary Examiner* — Jessica Yuen

(57) ABSTRACT

A shoe deodorizing degerming dehumidifier includes a housing, a main control circuit installed in the housing, a fan and an ozonizer. The housing is detachable from the shoes and is in a shape suitable for putting into and out from the shoe cavity. The housing is provided with an air inlet and an air outlet. The ozonizer is used for producing ozone for sterilizing in the shoe cavity. The fan is used for pushing air into the air inlet and draining the air from the air outlet, so as to promote ventilation in the shoe cavity. The shoe deodorizing degerming dehumidifier can be detached from a shoe and used repeatedly. Compared with prior shoe and deodorant degerming product, this product is more convenient in use, easier for maintenance, more environment friendly, more energy saving, and may reduce the purchase cost of the buyer.

9 Claims, 3 Drawing Sheets

(56) References Cited

U.S. PATENT DOCUMENTS

2005/0126033 A1    6/2005  Macher
2015/0008336 A1*  1/2015  Rubinchikov ............ A61L 2/10
                                                                  250/455.11

FOREIGN PATENT DOCUMENTS

| CN | 201996510 U | | 10/2011 |
| CN | 203872071 U | * | 10/2014 |
| CN | 104491900 A | | 4/2015 |
| JP | 09172955 A | * | 7/1997 |

* cited by examiner

SHOE DEODORIZING DEGERMING DEHUMIDIFIER AND SHOE DEODORIZING DEGERMING DEHUMIDIFYING METHOD

CROSS-REFERENCE TO RELATED APPLICATIONS

The present application is a Continuation Application of PCT application No. PCT/CN2015/081014 filed on Jun. 8, 2015, which claims the benefit of Chinese Patent Application No. 201410790351.7 filed on Dec. 17, 2014, the contents of which are hereby incorporated by reference.

FIELD

The present application relates to a shoe deodorizing degerming dehumidifier.

BACKGROUND

With the improvement of people's living standard, people pay more and more attention to the details of living, especially in personal health care and personal hygiene, so people have higher requirement on shoes cleaning (including deodorizing, degerming, dehumidifying). According to prior shoes with ozone sterilizing function, the sterilizing unit is fixed on the shoes, and is used only for this shoe and cannot be used for other shoes. That is to say, when this pair of shoes is broken, the deodorizing unit is also discarded. This causes a waste of resource and a limitation of usage degree. In addition, prior product produces ozone continuously, i.e. the product always produces ozone once the product is started. This may cause that the ozone exceeds the allowed limit in some area. The ozone, once exceeding the allowed limit, is harmful to human body, and detriment to the user's health, and also wastes energy and resources.

SUMMARY

The main object of the present application is to provide a shoe deodorizing degerming dehumidifier to overcome the shortcomings of the priorprior art, have deodorizing, degerming, dehumidification functions on the shoes, realizing multi-purposes by a single device, with high usage efficiency, convenient and flexible, also good at energy saving.

Another object of the present application is to provide a shoe deodorizing degerming dehumidifying method with this shoe deodorizing degerming dehumidifier to overcome the shortcomings of the prior artprior.

For the objects above, the present application provides following technical solutions:

A shoe deodorizing degerming dehumidifier, including: a housing, a main control circuit installed in the housing, a fan and an ozonizer. The power supply input end of the main control circuit is used to connect the power supply. Different output ends of the main control circuit are connected respectively with the fan and the ozonizer. The housing is detachable from a shoe and is in a shape suitable for putting into and out a shoe cavity of the shoe. The housing is provided with an air inlet and an air outlet. The ozonizer is used for producing ozone for sterilizing in the shoe cavity. The fan is used for pushing air into the air inlet and draining the air from the air outlet, so as to promote ventilation in the shoe cavity.

In some preferred embodiments, the housing is in a shape having a longer size in longitudinal direction and a shorter size in transverse direction. The air inlet and the air outlet are located respectively at two longitudinal ends of the housing.

In some preferred embodiments, the housing is in a streamlined shape similar to a computer mouse.

In some preferred embodiments, the fan is near the air outlet. The ozonizer is located between the air inlet and the fan.

In some preferred embodiments, the power supply includes a battery installed inside the housing.

In further preferred embodiments, the battery is rechargeable. The housing is provided with a charging port. The charging port is preferred to be USB port.

In some preferred embodiments, the housing is provided with a switch connected to the main control circuit.

In some preferred embodiments, the shoe deodorizing degerming dehumidifier further includes a voltage boost circuit installed in the housing. The main control circuit is connected to the ozonizer through the voltage boost circuit.

In some preferred embodiments, the shoe deodorizing degerming dehumidifier will operate at least for one working cycle once it is turned on. In each working cycle, under the control of the main control circuit, the ozonizer operates at a first work stage, and then the fan operates at a second work stage.

In further preferred embodiments, the duration of the first work stage is 20-40 minutes and the duration of the second work stage is 10-40 minutes.

In further preferred embodiments, the first stage work includes at least one intermittent working cycle of the ozonizer. During the intermittence working cycle of the ozonizer, the ozonizer turns on first for a period of time and then turns off for a period of time.

Preferably, the ozonizer turns on first for a period of time to reach an ozone concentration sufficient for deodorizing and degerming in the shoe cavity.

In further preferred embodiments, the duration of the first work stage is 20-40 minutes and the duration of the second work stage is 10-40 minutes. The first work stage includes two intermittent working cycles of the ozonizer. In each intermittence working cycle of the ozonizer, the ozonizer turns on first for 3-10 minutes and then turns off for 5-15 minutes.

In further preferred embodiments, the shoe deodorizing degerming dehumidifier will operate only for one working cycle once it is turned on, and then turn off until next turn-on.

On the other hand, the present application also provides a shoe deodorizing degerming dehumidifying method. This shoe deodorizing degerming dehumidifier can work according to the any control mode mentioned in the embodiments above.

In some preferred embodiments, the shoe deodorizing degerming dehumidifier works at least for one working cycle once it is turned on. In each working cycle, under the control of the main control circuit, the ozonizer operates at a first work stage, and then the fan operates at a second work stage.

In further preferred embodiments, the duration of the first work stage is 20-40 minutes and the duration of the second work stage is 10-40 minutes.

In further preferred embodiments, the first stage work includes at least one intermittent working cycle of the ozonizer. During the intermittence working cycle of the ozonizer, the ozonizer turns on first for a period of time and then turns off for a period of time.

Preferably, the ozonizer turns on first for the period of time to reach an exact ozone concentration sufficient for deodorizing and degerming the shoe cavity.

In further preferred embodiments, the duration of the first work stage is 20-40 minutes and the duration of the second work stage is 10-40 minutes. The first work stage includes two intermittent working cycles of the ozonizer. In each intermittence working cycle of the ozonizer, the ozonizer turns on first for 3-10 minutes and then turns off for 5-15 minutes.

In further preferred embodiments, the shoe deodorizing degerming dehumidifier will work only for one working cycle once it is turned on, and then turn off until next turn-on.

The shoe deodorizing degerming dehumidifier disclosed in this application produces ozone and ventilates air, deodorizing, degerming and dehumidifying the shoes at one time, thus combining the degerming function and dehumidifying function together. The design is more practical than the prior art. In this portable and detachable design, the shoe deodorizing degerming dehumidifier can be separated from a shoe and can be put directly into the shoe cavity. Therefore, the shoe deodorizing degerming dehumidifier disclosed in this application can be used repeatedly. Compared with the prior art having a shoe integrated with a deodorant degerming product, the shoe deodorizing degerming dehumidifier of the present application is more convenient in use, easier maintenance, more environment friendly, more energy saving, and may reduce effectively the purchase cost of the buyer. As the product is put directly into the shoe cavity, the deodorizing, degerming and dehumidifying effect is good. Preferably, the shoe deodorizing degerming dehumidifier works periodically with different stages to ensure the ozone will not be excessive and electric power will not be wasted so that it is more energy efficient and environmentally friendly than conventional products.

DETAILED DESCRIPTION

The embodiments of the present application are detailed below. It should be emphasized here that the following description is just exemplary and will not limit the scope and application of the present application.

Figure 1:
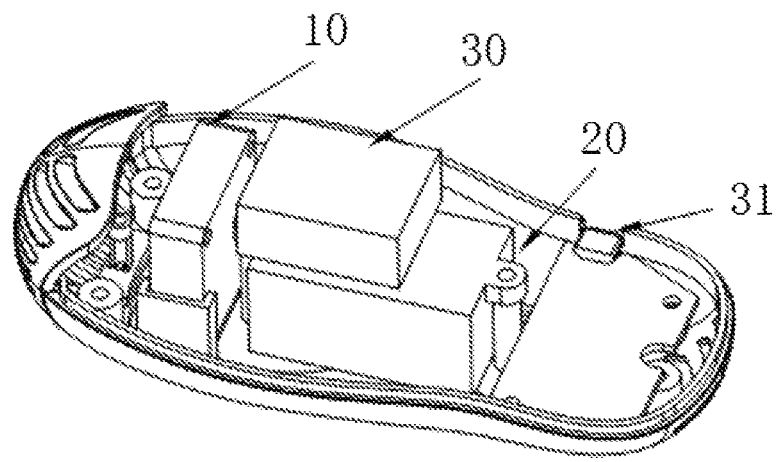
FIG. 1 is the internal structure view of one embodiment of the shoe deodorizing degerming dehumidifier disclosed in the present application.
Figure 2:
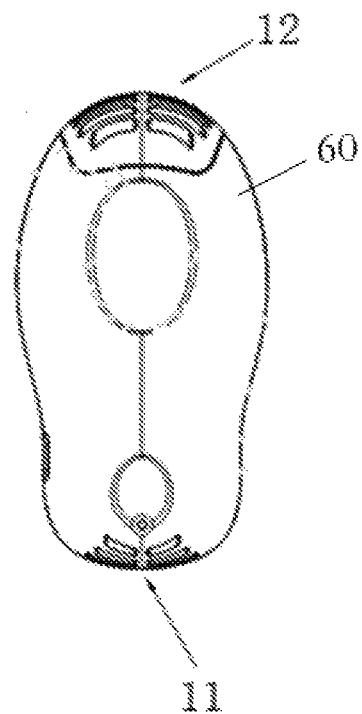
FIG. 2 is the top view of one embodiment of the shoe deodorizing degerming dehumidifier disclosed in the present application.
Figure 3:
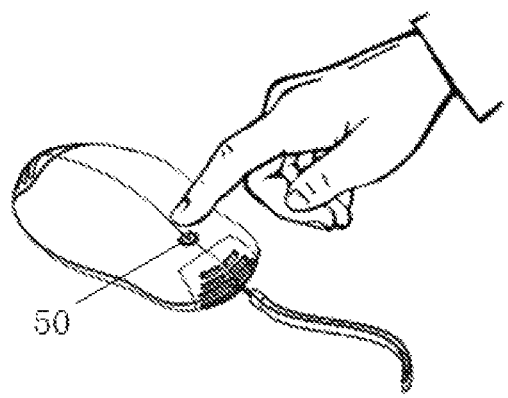
FIG. 3 is the view of the housing shape and switch structure of one embodiment of the shoe deodorizing degerming dehumidifier disclosed in the present application.
Figure 4:
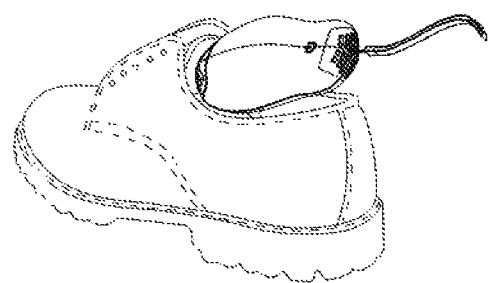
FIG. 4 is the operation illustration how the shoe deodorizing degerming dehumidifier is put into the shoe cavity in one embodiment disclosed in the present application.
Figure 5:
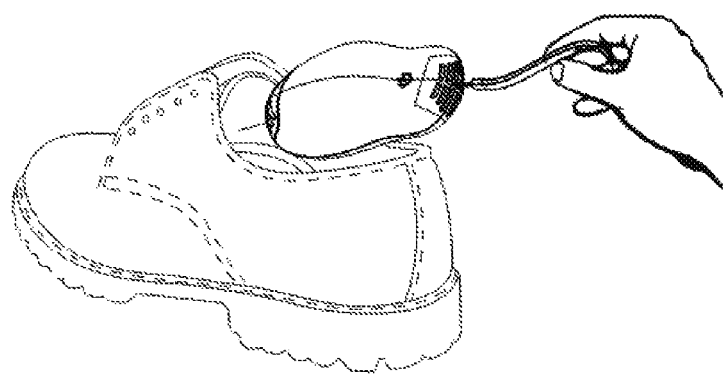
FIG. 5 is the operation illustration how the shoe deodorizing degerming dehumidifier is taken out from shoe cavity in one embodiment disclosed in the present application.
Figure 6:
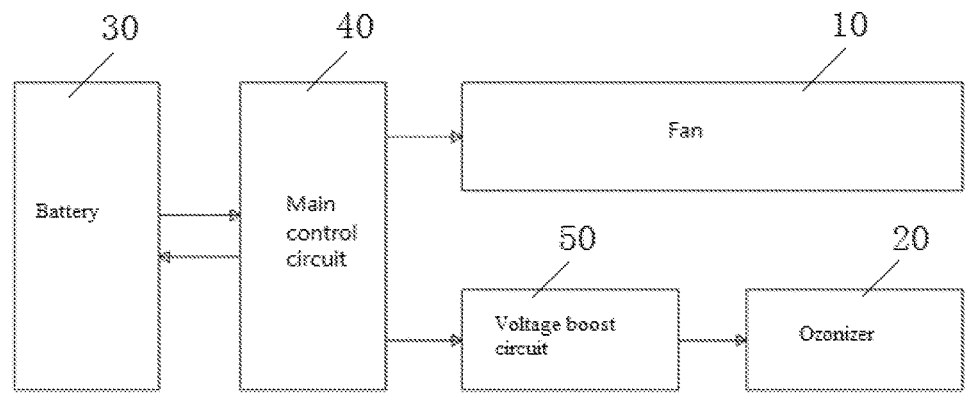
FIG. 6 is the electric circuit structure view of the shoe deodorizing degerming dehumidifier of one embodiment disclosed in the present application.
Figure 7:
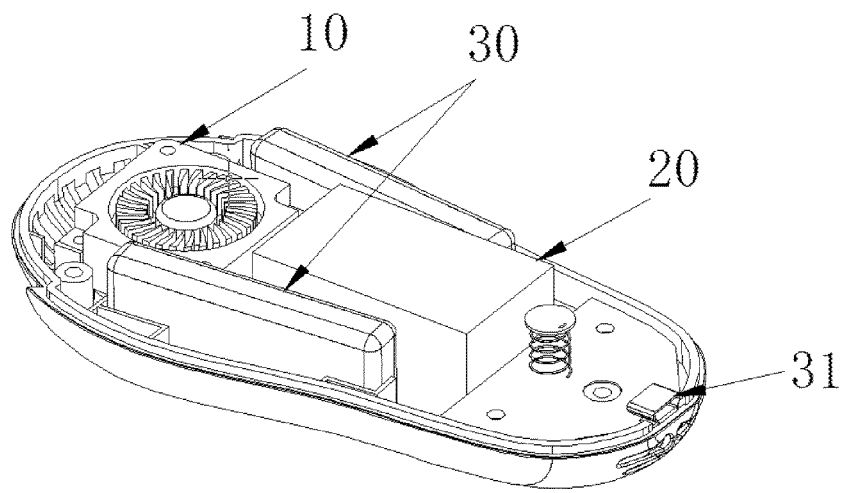
FIG. 7 is the internal structure view of the shoe deodorizing degerming dehumidifier of one embodiment disclosed in the present application.

Referring to FIG. 1 to FIG. 7, according to some embodiments of the present application, the shoe deodorizing degerming dehumidifier includes a housing 60, a main control circuit 40 installed in the housing 60, a fan 10 and an ozonizer 20. The power supply input end of the main control circuit 40 is used to connect the power supply. Different output ends of the main control circuit 40 are connected respectively with the fan 10 and the ozonizer 20. The housing 60 is detachable from a shoe and is in a shape suitable for putting into and out a shoe cavity of the shoe. The housing 60 is provided with an air inlet and an air outlet. The ozonizer 20 produces ozone for sterilizing in the shoe cavity. The fan 10 pushes air into the air inlet and drain air from the air outlet, so as to promote ventilation in the shoe cavity. The shoe deodorizing degerming dehumidifier in this embodiment of the present application combines deodorizing, degerming, dehumidifying functions together, and realizes multi-functions in a single device. The shoe deodorizing degerming dehumidifier of this embodiment of the present application can be separated from the shoe, unlike the prior art having a deodorizing dehumidifier integrated with a shoe. This shoe deodorizing degerming dehumidifier is an independent product and is portable. This product can be put into different shoes for deodorizing, degerming and dehumidifying, and does not need to be discarded when a pair of shoes is broken, so it saves resources and protects the environment. As this product can be put directly into the shoe cavity, the deodorizing, degerming, dehumidifying effect of this shoe deodorizing degerming dehumidifier is good. It is convenient for a user to use this shoe deodorizing degerming dehumidifier, as the shoe deodorizing degerming dehumidifier can be used in many shoes. For example, the user can put the shoe deodorizing degerming dehumidifier into the shoe taken off after coming home every day. Once started, the shoe deodorizing degerming dehumidifier performs automatically the functions of deodorizing, degerming and dehumidifying, and stops working after one or more working cycles. When the shoe deodorizing degerming dehumidifier finishes work in one shoe, it can be put into another shoe. When the shoe needs to be put on, the shoe deodorizing degerming dehumidifier can be taken out for use in next time. The detachable structure also facilitates the independent maintenance of the shoe deodorizing degerming dehumidifier. In a word, this detachable structure allows that the shoe deodorizing degerming dehumidifier can be used repeatedly. This product is flexible and convenient in use, extends the service life, reduces production cost, reduces waste and is environmentally friendly.

As shown in FIGS. 1 to 5, in some preferred embodiments, the housing 60 is a shape having a longer size in longitudinal direction and a shorter size in transverse direction. The air inlet 11 and the air outlet 12 are located respectively at two longitudinal ends of the housing 60. In some preferred embodiments, the housing 60 is in a streamlined shape similar to a traditional computer mouse. In some preferred embodiments, the fan 10 is near the air outlet 12. The ozonizer 20 is located between the air inlet 11 and the fan 10. According to the design above, the shoe deodorizing degerming dehumidifier can be put into and taken out conveniently from the shoe cavity, and can promote efficient air circulation. The structure also helps the ozone generated by the ozonizer 20 flow along with the air flow, so as to reaches every corner of the shoe cavity, thereby increasing the sterilizing and deodorizing effect.

The power supply can include a battery 30 installed inside the housing 60. The battery 30 is a rechargeable battery 30 and can be charged and used multiple times. The housing 60 is provided with a charging port. Preferably, the charging port is a USB port 31.

The housing 60 is provided with a switch 50 which is connected to the main control circuit 40. The user can press down the switch 50 to control conveniently the shoe deodorizing degerming dehumidifier.

In some preferred embodiments, the shoe deodorizing degerming dehumidifier can include also a voltage boost circuit installed in the housing 60. The main control circuit 40 is connected to the ozonizer 20 through the voltage boost circuit. The voltage boost circuit can boost the output voltage of the main control circuit 40, thereby providing enough high voltage to the ozonizer 20.

The main control circuit 40 manages the battery 30 on charging and discharging, and also controls the working hours and cycles of the fan 10, as well as the working time and working cycles of the voltage boost circuit.

In some preferred embodiments, the shoe deodorizing degerming dehumidifier operates at least for one working cycle once it is turned on. In each working cycle, under the control of the main control circuit 40, the ozonizer 20 operates at a first work stage, and then the fan 10 operates at a second work stage. Preferably, the duration of the first work stage is 20-40 minutes and the duration of the second work stage is 10-40 minutes.

In further preferred embodiments, the first stage work includes at least one intermittent working cycle of the ozonizer 20. During the intermittence working cycle of the ozonizer 20, the ozonizer 20 turns on first for a period of time and then turns off for a period of time. Preferably, the ozonizer 20 turns on first for a period of time to reach an ozone concentration sufficient for deodorizing and degerming in the shoe cavity.

In further preferred embodiments, the duration of the first work stage is 20-40 minutes and the duration of the second work stage is 10-40 minutes. The first work stage includes two intermittent working cycles of the ozonizer 20. In each intermittence working cycle of the ozonizer 20, the ozonizer 20 turns on first for 3-10 minutes and then turns off for 5-15 minutes.

In further preferred embodiments, the shoe deodorizing degerming dehumidifier will operate only for one working cycle once it is turned on, and then turn off until next turn-on.

In order to get better deodorizing, degerming and dehumidifying effect, and do not produce excessive ozone, not waste energy, the shoe deodorizing degerming dehumidifier is preferred to work in an intermittent mode. For example, after turning on the shoe deodorizing degerming dehumidifier, the ozonizer 20 produces ozone for 10-20 minutes first, and then it performs deodorizing and degerming for 30 minutes. After that, the fan 10 begins dehumidifying and ventilation. After the fan 10 works for 30 minutes for ventilation, the work is finished completely. That is a complete working cycle. Preferably, the product can be set up that it can begin a new working cycle only after it is turned on again manually.

In another example, after the shoe deodorizing degerming dehumidifier starts, the ozonizer 20 produces ozone for 5 minutes and stops working for 10 minutes, and generates ozone for 5 minutes again, and then stops working for 10 minutes. Finally the fan 10 works for 30 minutes for dehumidifying. After that, one working cycle is completed. The product can begin next working cycle only after it is turned on manually. Due to less air flow in the shoe, every time the ozonizer 20 stops work for 10 minutes, the concentration of ozone can have effective deodorizing and degerming effect. In such an intermittent work mode, the ozone will not be excessive, and electricity will not be wasted, but with similar deodorizing and degerming effect.

The main control circuit 40 can boost the voltage of the voltage boost circuit up to 1-5 KV during work, and then supply the boosted power to the ozonizer 20 to generate ozone, thereby achieving deodorizing and degerming effect. At the same time, the battery 30 also provides electric power to the fan 10 to circulate air and take away the moisture from the shoe, thereby achieving dehumidifying effect. The fan 10 also helps the ozone go to every corner of the shoe, and circulate air effectively in the shoe after deodorizing and degerming, so as to keep the shoe inside dry and clean. The ozonizer 20 produces ozone for deodorizing and sterilizing. After the user presses down the switch 50 and puts the shoe deodorizing degerming dehumidifier into the shoe, one working cycle begins. The main control circuit 40 controls entire working cycle. First, it provides the electric power to the voltage boost circuit, and then high voltage power is provided to the ozonizer 20 to generate ozone. The fan 10 does not work during this period of time. After the ozone reaches a concentration sufficient for deodorizing and degerming inside the shoe, the ozonizer 20 stops working. The ozone is kept in every corner of the shoe for a period of time for deodorizing and degerming, so as to eliminate the odor and bacteria. The process above is one intermittence working cycle of the ozonizer, and it can be repeated by one or more times. After that, the fan 10 works to take away all moisture inside the shoe and keep the shoe inside dry and clean. Thus a complete working cycle is finished. At the end of the working cycle, the shoe deodorizing degerming dehumidifier can be taken out from the shoe.

The content above is the detailed description of the present application with the specific/preferred embodiments and shall not be believed that the specific embodiments of the present application are only limited to this content. Those skilled in the art, under the precondition without departing from the concept of the application, can also make alternative modes or modification on the embodiments described, but these alternative or modification modes should be regarded to be within the protection scope of the present application.

What is claimed is:

1. A shoe deodorizing, degerming and dehumidifying method wherein a shoe deodorizing degerming dehumidifier is used for shoe deodorizing, degerming and dehumidifying, the shoe deodorizing degerming dehumidifier comprising a housing, a main control circuit installed in the housing, a fan and an ozonizer, wherein a power supply input end of the main control circuit is used to connect a power supply, and different output ends of the main control circuit are connected respectively with the fan and the ozonizer, wherein the housing is detachable from the shoes and is in a shape suitable for putting into and out a shoe cavity of the shoe cavity, and the housing is provided with air inlet and air outlet, wherein the ozonizer is used for producing ozone for sterilizing in the shoe cavity, and the fan is used for pushing air into the air inlet and drains the air from the air outlet, so as to promote ventilation in the shoe cavity, wherein the shoe deodorizing degerming dehumidifier operates at least for one working cycle once it is turned on, wherein in each working cycle, under the control of the main control circuit, the ozonizer operates at a first work stage, and then the fan operates at a second work stage, wherein the duration of the first work stage is 20-40 minutes and the duration of the second work stage is 10-40 minutes, wherein the first work stage comprises two intermittent working cycles of the ozonizer, wherein in each intermittence working cycle of the ozonizer, the ozonizer turns on first for 3-10 minutes to reach an ozone concentration sufficient for deodorizing and degerming in the shoe cavity and then turns off for 5-15 minutes.

2. The shoe deodorizing, degerming and dehumidifying method according to claim 1, wherein the housing is a shape longer in longitudinal direction and shorter in transverse direction, and the air inlet and air outlet are located respectively at both longitudinal ends of the housing.

3. The shoe deodorizing, degerming and dehumidifying method according to claim 2, wherein the housing is in a streamlined shape similar to a computer mouse.

4. The shoe deodorizing, degerming and dehumidifying method according to claim 1, wherein the fan is near the air outlet and the ozonizer is located between the air inlet and the fan.

5. The shoe deodorizing, degerming and dehumidifying method according to claim 1, wherein the power supply comprises a battery installed inside the housing.

6. The shoe deodorizing, degerming and dehumidifying method according to claim 5, wherein the battery is rechargeable and the housing is provided with a charging port.

7. The shoe deodorizing, degerming and dehumidifying method according to claim 1, wherein the housing is provided a switch which is connected to the main control circuit.

8. The shoe deodorizing, degerming and dehumidifying method according to claim 1, wherein it further comprises a voltage boost circuit installed in the housing, wherein the main control circuit is connected to the ozonizer through the voltage boost circuit.

9. The shoe deodorizing, degerming and dehumidifying method according to claim 1, wherein the shoe deodorizing degerming dehumidifier will operate only for one working cycle once it is turned on, and then turn off until next turn-on.

* * * * *